(12) United States Patent
Son et al.

(10) Patent No.: US 8,663,664 B2
(45) Date of Patent: Mar. 4, 2014

(54) TEMPERATURE SENSITIVE STATE-CHANGING HYDROGEL COMPOSITION AND METHOD FOR THEIR PREPARATION

(75) Inventors: Tae-Won Son, Daegu (KR); Young-Hun Kim, Daegu (KR); Hyun-Oh Yoo, Seoul (KR)

(73) Assignee: Genic Co., Ltd (KR)

( * ) Notice: Subject to any disclaimer, the term of this patent is extended or adjusted under 35 U.S.C. 154(b) by 438 days.

(21) Appl. No.: 10/567,483

(22) PCT Filed: Sep. 13, 2004

(86) PCT No.: PCT/KR2004/002034
§ 371 (c)(1),
(2), (4) Date: May 21, 2007

(87) PCT Pub. No.: WO2005/016305
PCT Pub. Date: Feb. 24, 2005

(65) Prior Publication Data
US 2007/0280974 A1 Dec. 6, 2007

(30) Foreign Application Priority Data
Aug. 14, 2003 (KR) .......................... 10-2003-0056557

(51) Int. Cl.
*A61K 8/02* (2006.01)
*A61K 35/26* (2006.01)

(52) U.S. Cl.
USPC .......................................... 424/401; 426/578

(58) Field of Classification Search
USPC .......................................................... 424/401
See application file for complete search history.

(56) References Cited

U.S. PATENT DOCUMENTS

| | | | |
|---|---|---|---|
| 4,291,025 A | 9/1981 | Pellico | |
| 4,517,216 A | 5/1985 | Shim | |
| 4,593,053 A | 6/1986 | Jevne et al. | |
| 4,942,158 A | 7/1990 | Sarpotdar et al. | |
| 4,983,385 A * | 1/1991 | Hasegawa et al. | 514/772.4 |
| 5,064,654 A | 11/1991 | Berner et al. | |
| 5,344,655 A | 9/1994 | Sakai et al. | |
| 5,405,366 A | 4/1995 | Fox et al. | |
| 5,840,338 A | 11/1998 | Roos et al. | |
| 5,958,420 A * | 9/1999 | Jenson | 424/771 |
| 6,107,537 A * | 8/2000 | Elder et al. | 604/364 |
| 6,361,790 B1 | 3/2002 | Rolf et al. | |
| 6,406,712 B1 | 6/2002 | Rolf | |
| 6,664,301 B1 * | 12/2003 | Kross | 516/105 |
| 2002/0159982 A1 | 10/2002 | Bonassar | |
| 2003/0113356 A1 | 6/2003 | Deckner | |
| 2005/0037079 A1* | 2/2005 | Son et al. | 424/486 |

FOREIGN PATENT DOCUMENTS

| | | |
|---|---|---|
| EP | 04774311 | 11/2010 |
| JP | 60-246314 | 12/1985 |
| JP | 63-104914 | 5/1988 |
| JP | 03-081213 | 4/1991 |
| JP | 08-290051 | 11/1996 |
| JP | 2003-113036 | 4/2003 |
| WO | WO 02/076518 A1 | 10/2002 |

OTHER PUBLICATIONS

Kang Wang, Zhimin He: "Alginate-konjac glucomannan-chitosan breads as controlled release matrix" International Journal of Pharmaceutics, vol. 244, Sep. 5, 2002, pp. 117-126, p. 119, left-hand column-p. 123, left-hand column.
US 6,214,374, 04/2001, Schmirler et al. (withdrawn)

* cited by examiner

*Primary Examiner* — Layla Soroush
(74) *Attorney, Agent, or Firm* — Wells St. John P.S.

(57) ABSTRACT

The object of this invention is to provide a temperature-sensitive state-changing hydrogel composition and a method of producing the same. The hydrogel composition includes 1-10 wt % of branched gelation polymer, 0.5 5 wt % of electrolyte gelation polymer, 0.5-5 wt % of skin-communication enhancer, 1-10 wt % of natural biomaterial, 3-30 wt % of polyhydric alcohol, 1-10 wt % of functional additive, and 30-93 wt % of water based on a total weight of the composition. Hydrogel is transformed into a fluid state at 10-50° C. The hydrogel composition is transformed into a fluid state due to body temperature when it comes into contact with the skin to be fluidized, so that cosmetics or drugs contained in hydrogel are uniformly and quickly delivered into the skin.

2 Claims, 3 Drawing Sheets

TEMPERATURE SENSITIVE STATE-CHANGING HYDROGEL COMPOSITION AND METHOD FOR THEIR PREPARATION

RELATED PATENT DATA

This application claims priority to Patent Cooperation Treaty application Serial No. PCT/KR2004/002034, which was filed Aug. 13, 2004, and which claims priority to Korean Application Serial No. 2003-56557, which was filed Aug. 14, 2003.

TECHNICAL FIELD

The present invention relates, in general, a temperature-sensitive state-changing hydrogel composition and a method of preparing the same and, more particularly, to a temperature-sensitive state-changing hydrogel composition, which is transformed, depending on temperature, from a gel state to a fluid state to be cosmetically and efficiently applied to skin, and a method of preparing the same.

BACKGROUND ART

A state-changing hydrogel composition means a hydrogel material, which contains a great quantity of water, and is suddenly transformed into a fluid state at a certain temperature.

In recent years, skin treatment using hydrogel has been applied in many areas such as cosmetic products, skincare, dermal beauty and dermal therapy. Hydrogel is well known as a material suitable to be used as a matrix for the controlled release of drugs (N. A. Pappas Ed., "Hydrogels in Medicine and Pharmacy, Vol. 11; Polymers", CRC Press, Inc., 1987). This means that hydrogel as the matrix is used as a drug delivery body containing hormones such as progesterone therein to slowly release the hormones into the body, thereby controlling the quantity of the hormones. U.S. Pat. No. 5,344,655 by Sakai et al. discloses a technology of transdermally delivering drugs into the body using a hydrogel matrix containing water soluble polymers such as cellulose derivatives. In U.S. Pat. No. 5,405,366 by Fox et al., the use of adhesive hydrogel which forms an optical bridge and contains water soluble polymers in a transdermal drug delivery system is disclosed. U.S. Pat. No. 4,593,053 by Gebner et al. discloses the usage and production method of hydrogel that is friendly to skin and pressure sensitive. Transdermal delivery of drugs is a technique that transfers hormones such as Progesterone, Progestin, Estrogen, and Testosterone into the body through the skin. This sophisticated medicating system slowly and transdermally releases the predetermined quantity of medicine from hydrogel which adheres to the skin into body. U.S. Pat. No. 6,214,374 by Shumiller et al. introduces a composition of hydrogel for efficient transdermal delivery of drugs without being blocked by the skin, and a method and a device for producing the same. U.S. Pat. No. 5,064,654 by Verner et al. also discloses a composition of adhesive hydrogel for the transdermal delivery of drugs. U.S. Pat. No. 4,942,158 by Sapota et al. discloses a composition of hydrogel that contains a permeation enhancer for improved transdermal delivery of drugs. Moreover, U.S. Pat. Nos. 6,361,790 and 6,406,712 by Rolf et al. disclose a method of applying a dressing and a patch to the skin using hydrogel.

In all of the above conventional techniques, hydrogel is applied to the skin, but hydrogel only has a function of slowly releasing the drugs contained in hydrogel, acting as a matrix to the skin, while it is maintained in a gel state.

Meanwhile, when the drug delivery to the skin is controlled while hydrogel is kept in the gel state, there are inevitable disadvantages, namely, that it takes a relatively long time for the drugs to permeate through the skin, and that the drugs are delivered only to the portion of the skin with which the hydrogel comes into direct contact. Conventionally, every possible effort was made to add a permeation enhancer to hydrogel or to produce hydrogel that is friendly to the skin so as to overcome the disadvantages.

Generally, unlike medical treatment of a skin wound, when cosmetic products are used for skincare, a protection device must not adhere to the skin for a long time, but for a short period and subsequently be removed. Hydrogel is used to improve the effectiveness of skincare, and is produced in a form of a sheet or a patch to be effectively applied to the skin. However, even though the above hydrogel products are employed, if hydrogel is in a gel state, there is a limit in communication between hydrogel and the skin, and thus, it is impossible to assure a desirable quantity and speed of a cosmetic delivered from hydrogel to the skin.

Communication between hydrogel and the skin greatly affects the delivery of cosmetics or drugs contained in hydrogel to the skin. In other words, greater communication brings about easier and faster delivery of the cosmetics or drugs from hydrogel to the skin, but lesser communication causes less effective and slower delivery.

Furthermore, when hydrogel containing cosmetics is used for skincare, hydrogel adhering to the skin must be removed within a relatively short time in comparison with use of medical drugs for treatment, and thus, it is required that the cosmetics be rapidly delivered to the skin. In other words, the cosmetics contained in hydrogel applied to the skin for skincare must be quickly delivered from hydrogel to the skin in a great amount. To fulfill this feature, hydrogel must have a characteristic capable of quickly and uniformly delivering the cosmetics into the skin unlike conventional hydrogel, and thus, there remains a need to develop innovative hydrogel that can fulfill the above characteristics.

DISCLOSURE OF THE INVENTION

Accordingly, an object of the present invention is to provide a temperature-sensitive state-changing hydrogel composition, which is transformed into a fluid state by a body temperature after it comes into contact with the skin to be fluidized so as to quickly and uniformly deliver a cosmetic into the skin.

Another object of the present invention is to provide a method of producing a temperature-sensitive state-changing hydrogel composition which uniformly and quickly permeates into the skin.

In order to accomplish the above objects, the present invention provides a temperature-sensitive state-changing hydrogel composition, which includes 1-10 wt % of branched gelation polymer, 0.5-5 wt % of electrolyte gelation polymer, 0.5-5 wt % of skin-communication enhancer, 1-10 wt % of natural biomaterial, 3-30 wt % of polyhydric alcohol, 1-10 wt % of functional additive, and 30-93 wt % of water based on a total weight of the composition. Hydrogel is transformed into a fluid state at 10-50° C.

Furthermore, the present invention provides a method of producing a temperature-sensitive state-changing hydrogel composition, which includes mixing 1-10 wt % of branched gelation polymer selected from the group consisting of galactomannan, glucomannan, guar gum, locust bean gum and pluronic, 0.5-5 wt % of electrolyte gelation polymer selected from the group consisting of agar, algin, carrageenan, xanthan and gelan, 1-10 wt % of functional additive selected from the group consisting of chitosan, chitosan derivatives, proteoglycans, elastin, collagen, and hyaluronic acid, and 3-30 wt % of polyhydric alcohol, with each other, and adding 30-93 wt % of water to a mixture at room temperature, and subsequently heating the resulting mixed solution to 45-95° C. to produce a gel solution; and sequentially adding 1-10 wt % of natural biomaterial extracted from aloe, green tea, ginseng, wood vinegar, pine needles, gingko leaves, propolis, mulberry leaves, or silkworms, and 0.5-5 wt % of skin-communication enhancer selected from the group consisting of methylparaben, propylparaben, kojic acid, α-hydroxy acid, and retinol to the gel solution while maintaining the gel solution at 45-95° C., and cooling the resulting gel solution to room temperature.

BRIEF DESCRIPTION OF THE DRAWINGS

FIGS. 2a and 2b show two types of gelation polymers constituting a hydrogel according to the present invention, in which FIG. 2a shows gel-state polymer chains where an electrical bond of electrolyte gelation polymers and a physical bond of branched gelation polymers coexists, and FIG. 2b shows fluid-state polymer chains where the electrical bond of the electrolyte gelation polymers exists but the physical bond of the branched gelation polymers does not; and FIGS. 3a and 3b show a hydrogel sheet for skincare prepared using a hydrogel composition of the present invention, in which FIG. 3a is a rayon network textile used as a core, and FIG. 3b is hydrogel according to the present invention.

BEST MODE FOR CARRYING OUT THE INVENTION

Figure 1:
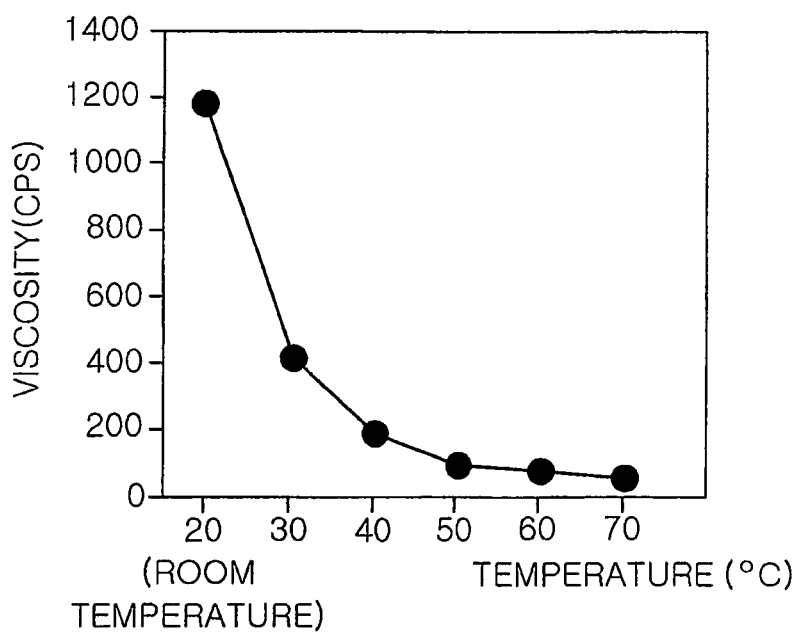
FIG. 1 is a graph showing viscosity as a function of temperature for a hydrogel composition according to the present invention.

Hereinafter, a detailed description will be given of the present invention.

A temperature-sensitive state-changing hydrogel composition according to the present invention is characterized in that it is transformed from a gel state to a fluid state at 10-50° C., and preferably a temperature range which approaches body temperature (30-40° C.) so as to desirably improve the communication between the skin and hydrogel and to quickly deliver a great amount of cosmetics or drugs from the hydrogel composition to the skin due to an enhancer added to the composition.

The present invention provides an ideal and effective method of employing hydrogel for skincare that can be used for a relatively short time, and a novel temperature-sensitive state-changing hydrogel composition suitable to the method.

The temperature-sensitive state-changing hydrogel composition according to the present invention is transformed from the gel state to the fluid state by body temperature when a hydrogel sheet or patch containing a beauty product is applied to the skin, thereby improving communication between the fluid hydrogel composition and skin. Consequently, the cosmetics smoothly permeate into the skin. Furthermore, since a natural skin-communication enhancer for promoting the delivery of the cosmetics to the skin is contained in the hydrogel composition, a desirable amount of cosmetics is delivered quickly into the skin. Therefore, the present invention provides a novel hydrogel composition which is sensitive to a temperature variance and transformed from the gel state to the fluid state when it reaches a certain temperature.

The temperature-sensitive state-changing hydrogel according to the present invention has a physical property that the gel state, i.e. solid phase, is transformed into the fluid state, i.e. liquid phase, with an increase in temperature. Especially, when hydrogel sheet or patch products of the present invention used for skincare adhere to the skin, their temperatures increase due to the body temperature, and thus, hydrogel is transformed from the gel state to the fluid state. Thereby, the fluid composition spontaneously adheres to the skin and permeates into the skin, significantly improving communication between the skin and the composition.

To fulfill the above characteristics, the state-changing hydrogel composition of the present invention includes a gel forming substance having a branched polymer and an electrolyte polymer, a skin-communication enhancer capable of improving communication between the skin and composition, and a natural biomaterials. Also, polyhydric alcohol and a functional additive acting as a functional substance are contained in the composition to provide fluidity to the composition so that the hydrogel composition liquefied due to the body temperature adheres to the skin and permeates into the skin when the hydrogel is applied to the skin.

The hydrogel composition according to the present invention includes 1-10 wt % of branched gelation polymer, 0.5-5 wt % of electrolyte gelation polymer, 0.5-5 wt % of skin-communication enhancer, 1-10 wt % of natural biomaterial, 3-30 wt % of polyhydric alcohol, 1-10 wt % of functional additive and 30-93 wt % of water based on the total weight of the composition.

The present inventors found out that when the above stated ingredients are included in hydrogel composition in the above mentioned proportion, the hydrogel composition is transformed into a fluid state due to the body temperature when it is applied to the skin. It was also found that because of the above characteristics, the ingredients included in the hydrogel composition rapidly adhere to and permeate into the skin.

Figure 2A:
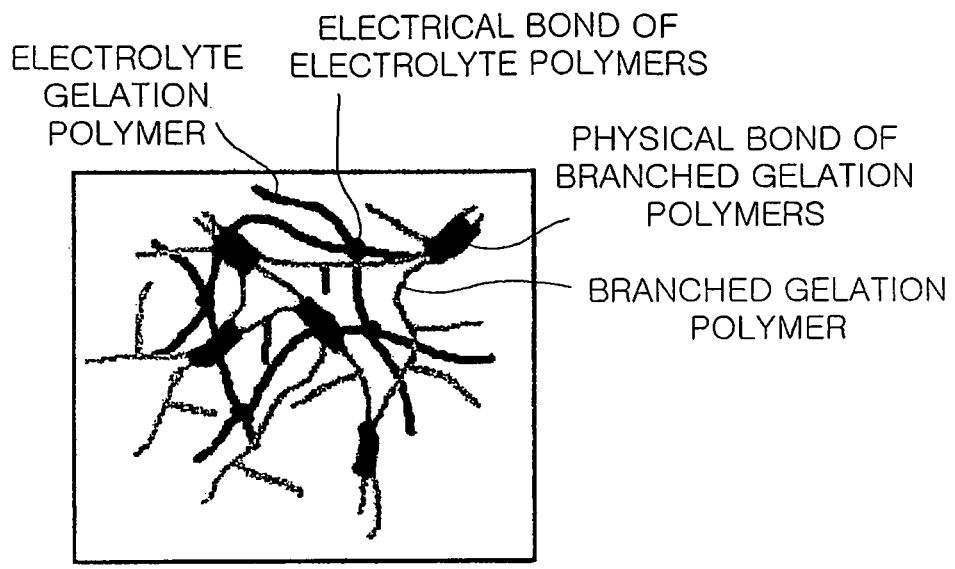
Figure 2B:
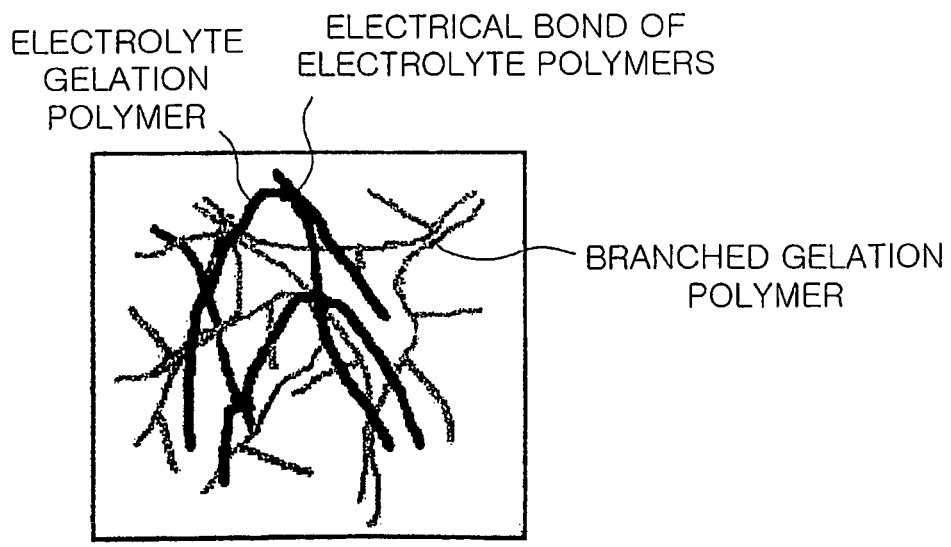

In the hydrogel composition of the present invention, the branched gelation polymer and electrolyte gelation polymer are used as the gel forming substance. In this regard, the electrolyte gelation polymer maintains the composition of the present invention in the gel state, and in some cases it keeps the composition of the present invention to stay in the gel state at room temperature (about 20° C. or so), preferably 0-30° C. Additionally, the branched gelation polymer functions to transform hydrogel in a solid state into the fluid state when the temperature increases to 10-50° C., preferably about 30-40° C., that is, similar to body temperature. With respect to this, FIG. 2 shows the gel including the two types of gelation polymers. At this time, FIG. 2a shows gel-state polymer chains where an electrical bond of electrolyte gelation polymers and a physical bond of branched gelation polymers coexists, and FIG. 2b shows fluid-state polymer chains where the electrical bond of the electrolyte gelation polymers exists but the physical bond of the branched gelation polymers does not.

The branched gelation polymer available to the present invention is a water soluble polysaccharide polymer which may be exemplified by galactomannan, glucomannan, guar gum, locust bean gum and pluronic. Furthermore, the electrolyte gelation polymer available to the present invention is a polysaccharide electrolyte polymer which may be exemplified by agar, algin, carrageenan, xanthan and gelan. At this time, the branched gelation polymer and electrolyte gelation polymer are contained in a content of 1-10 wt % and 0.5-5 wt %, respectively, based on the total weight of the composition. If the content deviates from the above range, gel may not be formed or the gel state may not be transformed into the fluid state even though the temperature increases.

The skin-communication enhancer is a material functioning to improve communication between the composition and skin to help a large amount of cosmetics or drugs to rapidly penetrate from the hydrogel composition into the skin. Illustrative, but non-limiting examples of the skin-communication enhancer include polysaccharides, such as chitosan, proteoglycans, chitosan derivatives, elastin, collagen, hyaluronic acid, or water soluble proteins, and it is preferable that its content be 0.5-5 wt % based on the total weight of the composition. When the content of the skin-communication enhancer is excessively low, its effect is insignificant, and when the content is excessively high, the gel state may be not transformed into the fluid state even though the temperature increases.

Similarly, the natural biomaterial is a material serving to improve communication between the skin and composition, and a natural material extracted from plants, animals or minerals. Non-limiting, illustrative examples of the natural biomaterial include extracts of aloe, green tea, ginseng, wood vinegar, pine needles, propolis, gingko leaves, silkworms, or mulberry leaves, and its content is 1-10 wt % based on the total weight of the composition. When the content of the natural biomaterial is excessively low, its effect is insignificant, and when the content is excessively high, the gel state may not be transformed into the fluid state even though the temperature increases.

Polyhydric alcohol is a material for helping the hydrogel composition of the present invention adhere to and permeate into the skin, in a form of water soluble liquid, and is exemplified by propylene glycol and glycerine, and its content is 3-30 wt % based on the total weight of the composition. When the content of polyhydric alcohol is excessively low, the gel state is not transformed into the fluid state even though the temperature increases, and when the content is excessively high, gel may be not formed.

The functional additive is capable of providing stability and functionality to hydrogel, and is exemplified by methylparaben, propylparaben, kojic acid, α-hydroxy acid, imidazolidinylurea, Twin 80 and retinol. The functional additive is contained in a content of 1-10 wt % based on the total weight of the composition. When the content is excessively low, storage stability is reduced, prohibiting a long-term storage, and when the content is excessively high, the gel state may be not transformed into the fluid state even though the temperature increases.

Water is a main ingredient of the hydrogel composition, and its content is 30-93 wt % based on the total weight of the composition. When the content is excessively low, the gel state is not transformed into the fluid state even though the temperature increases, and when the content is excessively high, gel may be not formed.

The hydrogel composition of the present invention as described above is in the gel state at a temperature of 0-10° C., and transformed from the gel state into the fluid state at 10-50° C. Furthermore, the hydrogel composition of the present invention may be in the gel state at 0-30° C. or at room temperature, and in the fluid state at 20-40° C. according to a variation in content of the ingredients constituting the composition. As described above, the hydrogel composition of the present invention is sensitively transformed in terms of state depending on temperature, and thus, when it is applied to the skin, all of the ingredients for skincare contained in the hydrogel composition may uniformly and quickly come into close contact with the skin and permeate into the skin.

Meanwhile, the hydrogel composition of the present invention may be produced according to the following procedure.

First, the branched gelation polymer and electrolyte gelation polymer are mixed with polyhydric alcohol to produce a polymer mixed solution, the functional additive is dissolved in polyhydric alcohol to produce a functional solution, and the two solutions are then mixed with each other to produce a basic mixture solution. Subsequently, the basic mixture solution is mixed with deionized water and heated. While being maintained at 45-95° C., the heated solution is sequentially mixed with the skin-communication enhancer and the natural biomaterials to produce the hydrogel composition in the fluid state. At this time, the amount of each ingredient is the same as in the abovementioned description of the hydrogel composition of the present invention. Likewise, available examples of each ingredient are the same as in the abovementioned description.

Figure 3:
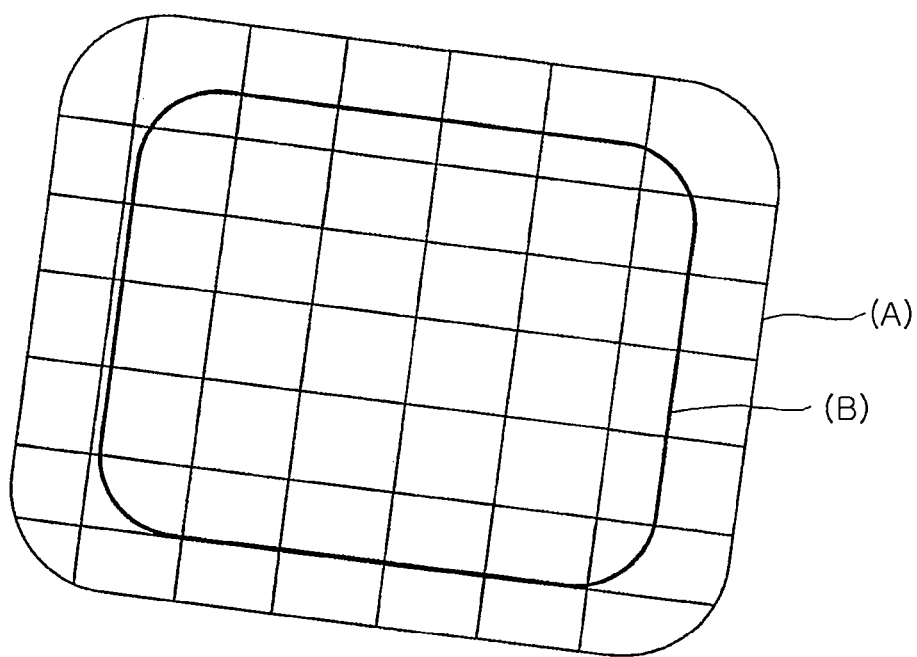

Furthermore, the hydrogel composition of the present invention may be produced in the form of a sheet or a patch to be used for skincare. For example, in order to use the hydrogel composition of the present invention for skincare, the fluid hydrogel composition is shaped into a sheet or a patch at a temperature of 30° C. or more, preferably 45-95° C., and then cooled to room temperature to produce the hydrogel composition in the gel state. FIGS. 3a and 3b show a hydrogel sheet for skincare prepared using the hydrogel composition of the present invention, in which a rayon network textile is employed as a core. FIG. 3a illustrates the rayon network textile, and FIG. 3b illustrates the hydrogel composition according to the present invention.

When the hydrogel sheet or patch of the present invention is applied to the skin, hydrogel is transformed from the gel state to the fluid state due to the body temperature. In other words, if the state-changing hydrogel composition of the present invention comes into contact with the skin, it is transformed into the fluid state due to body temperature. Thereby, the fluid composition spontaneously adheres to the skin and permeates into the skin, significantly improving communication between the skin and the composition. Consequently, a skincare effect is improved in comparison with a conventional hydrogel.

A better understanding of the present invention may be obtained through the following example which is set forth to illustrate, but is not to be construed as the limit of the present invention.

EXAMPLE 170 g of glycerine, 6 g of carrageenan and 20 g of locust bean gum were mixed at room temperature in a heating container of 3 liters while being agitated, and a solution in which 0.8 g of methylparaben and 0.3 g of propylparaben were dissolved in 30 g of glycerine was added to the mixture to produce a mixture solution. 740 g of deionized water was added to the mixture solution, and heated to 85° C. to produce a gel solution. 20 g of aloe extracts, 5 g of collagen, 2 g of imidazolidinylurea, 1.5 g of Twin 80, and 3.7 g of chitosan liquid were sequentially added to the gel solution while being maintained at 85° C. to produce a hydrogel composition. A viscosity variance of the hydrogel composition was measured according to temperature, and the results are shown in FIG. 1. From FIG. 1, it can be seen that the hydrogel composition is significantly reduced in viscosity with an increase in temperature, thereby being transformed into the fluid state.

A state-changing hydrogel sheet is produced by adding a rayon network textile as a wick to the hydrogel composition at 80° C. to be shaped into a sheet and then cooling the sheet to room temperature. This is a product used to control transdermal delivery of a cosmetic for skincare. Furthermore, when conventional hydrogel is applied to the skin, coverage is 40-70%, whereas hydrogel of the present invention has fluidity depending on temperature, and thus, it has a coverage of 100%. Additionally, since it has a fast migration rate of ingredients, epidermal absorption of hydrogel is improved.

INDUSTRIAL APPLICABILITY

As described above, the hydrogel composition of the present invention is not only very effective in skincare but also effective in skin treatment when rapid delivery of drugs is required or a skin-communication material is required. Especially, hydrogel of the present invention can be effectively used for skincare through a transdermal cosmetic delivery in which cosmetics are delivered from hydrogel to the skin.

The invention claimed is:

1. A transdermal cosmetic sheet comprising a rayon network textile as a wick, and a temperature-sensitive state-changing hydrogel composition thereupon, comprising:
   1-10 wt % of locust bean gum as a branched gelation polymer;
   0.5-5 wt % of carrageenan as an electrolyte gelation polymer;
   0.5-5 wt % of a mixture of chitosan and collagen;
   1-10 wt % of aloe extract;
   3-30 wt % of glycerine;
   0.46 wt % of at least one functional additive, the functional additive being an additive capable of providing stability to the hydrogel comprising methylparaben, propylparaben, and imidazlidinylurea; and
   remainder of water based on a total weight of the composition,
   wherein, the hydrogel is transformed into a fluid state at 30-50° C.

2. A method of producing a transdermal cosmetic sheet, comprising:
   Mixing 1-10 wt % of locust bean gum as a branched gelation polymer,
   0.5-5 wt % of carrageenan as an electrolyte gelation polymer,
   3-30 wt % of glycerine and
   0.46 wt % of at least one functional additive, the functional additive being an additive capable of providing stability to the hydrogel comprising methylparaben, propylparaben, and imidazlidinylurea, with each other;
   adding remainder of water to the mixture at room temperature;
   heating the resulting mixed solution to 45-95° C. to produce a gel solution;
   adding 0.5-5 wt % of a mixture of chitosan, and collagen and 1-10 weight % of aloe extract to the gel solution while maintaining the resulting hydrogel composition at 45-95° C.;
   adding a rayon network textile as a wick to the hydrogel composition at 80° C. to be shaped into a sheet and
   cooling the resulting sheet to room temperature, wherein the hydrogel composition has the ability to transform to a fluid state at a temperature between 30-50° C.

* * * * *

UNITED STATES PATENT AND TRADEMARK OFFICE
CERTIFICATE OF CORRECTION

PATENT NO. : 8,663,664 B2
APPLICATION NO. : 10/567483
DATED : March 4, 2014
INVENTOR(S) : Tae-Won Son, Young-Hun Kim and Hyun-Oh Yoo It is certified that error appears in the above-identified patent and that said Letters Patent is hereby corrected as shown below:

In the Specification

Column 1, line 17 – Replace "general, a" with --general, to a--

Column 1, line 54 – Replace "into body" with --into the body--

Column 5, line 16 – Replace "may be not" with --may not be--

In the Claims

Claim 2, Column 8, line 9 – Replace "Mixing" with --mixing--

Claim 2, Column 8, line 28 – Replace "sheet" with --sheet;--

Signed and Sealed this
Twenty-fourth Day of June, 2014

Michelle K. Lee
*Deputy Director of the United States Patent and Trademark Office*